United States Patent
Nakanishi et al.

(10) Patent No.: US 7,217,359 B2
(45) Date of Patent: May 15, 2007

(54) COLUMNS FOR CHROMATOGRAPH

(75) Inventors: Kazuki Nakanishi, Kyoto (JP);
Shigeru Hanzawa, Kamigahara (JP);
Yousuke Sato, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 80 days.

(21) Appl. No.: 10/894,222

(22) Filed: Jul. 19, 2004

(65) Prior Publication Data

US 2005/0023204 A1    Feb. 3, 2005

(30) Foreign Application Priority Data

Jul. 30, 2003    (JP) .................... P2003-203519

(51) Int. Cl.
*B01D 15/08*    (2006.01)
(52) U.S. Cl. .................... 210/198.2; 210/656
(58) Field of Classification Search ................ 210/635, 210/656, 659, 198.2
See application file for complete search history.

(56) References Cited

U.S. PATENT DOCUMENTS 5,624,875 A    4/1997    Nakanishi et al.

FOREIGN PATENT DOCUMENTS

| EP | 0 926 492 A1 | 6/1999 |
|---|---|---|
| JP | 61-265567 A1 | 11/1986 |
| JP | 03-285833 A1 | 12/1991 |
| JP | 06-265534 | 9/1994 |
| JP | 08-029952 B2 | 3/1996 |
| JP | 2004-115347 A1 | 4/2004 |
| RU | 2 060 498 C1 | 5/1996 |
| WO | WO 03/016859 A2 | 2/2003 |

OTHER PUBLICATIONS

Translation of Laureat: Alltech Produit: MCC, Colonne Multicapillaire, PTO 06-2289, Jan. 2006.*

"Catégorie <<Analyses Chimiques et Physico-Chimiques>> Lauréat : Alltech Produit : MCC, Colonne Multicapillaire" Mesures Regulaation Automatisme, CFE. Paris, France, No. 689, Nov. 1, 1996, p. 38, XP000679695.

Nakanishi, Kazuki, "Porous Gels Made By Phase Separation: Recent Progress and Future Directions," Journal of Sol-Gel Science and Technology, Kluwer Academic Publishers, Dordrecht, NL, vol. 19, No. 1-3, pp. 65-70.

* cited by examiner

*Primary Examiner*—Ernest G. Therkorn
(74) *Attorney, Agent, or Firm*—Burr & Brown

(57) ABSTRACT

The present invention provides a column for a liquid chromatograph having a honeycomb substrate including holes through which a sample flows and a separation phase filled in the holes. The separation phase is a porous bone structure composed of an inorganic material having open pores formed therein, and the porous bone structure is generated by a sol-gel transition process accompanied by a phase transition.

3 Claims, 5 Drawing Sheets

COLUMNS FOR CHROMATOGRAPH

This application claims the benefit of Japanese Patent Application P2003-203519, filed on Jul. 30, 2003, the entirety of which is incorporated by reference.

TECHNICAL FIELD OF THE INVENTION

The present invention relates to a column for a chromatograph.

BACKGROUND OF THE INVENTION

Related Art Statement

According to the multi-capillary column described in Japanese Patent publication 61-265567A, many capillaries each composed of a hollow fiber are bundled and bonded with each other by an adhesive to form a cylindrical article. It is thus possible to maintain the characteristic high performance of separation of a capillary column without causing diffusion into multi flow routes. The analysis can be made by means of a common HPLC system at the same time.

It is also known to manufacture porous bodies of silica using a sol-gel process by applying phase separation with a high reproducibility (see Japanese Patent 2123708B and Japanese Patent publication 3-285833A). According to the method, the uniformity of the shape and size distribution of holes can be considerably improved. It is also possible to form small holes each having a relatively large diameter. It is further described that the porous body is used as a separation phase of a column in Japanese Patent 3317749B.

According to the column described in Japanese Patent publication 61-265567A, it is necessary to increase the number of the capillaries and to bundle and bond many capillaries with each other by an adhesive, to improve the amount of a sample fluid subjected to processing and to use a common HPLC system. It is difficult, however, to bundle many capillaries in parallel with each other and then to bond them while their longitudinal directions are aligned on the same axis. That is, because each of the capillaries is not directly clamped, so that the longitudinal direction of each capillary is easily deviated from and inclined with respect to the axis. Excessive pressure may be thus applied onto each capillary so that the capillaries are easily deformed, curved, tipped and broken. The passing time of the sample solution in the capillaries may not be uniform and the sample solution may be leaked before the separation. The resolution of the separation of the column tends to be reduced.

An object of the present invention is to provide a column for a chromatograph having a structure that enables the separation of a sample, analysis by means of a common HPLC system and that provides superior resolution of separation.

SUMMARY OF THE INVENTION

The present invention provides a column for a chromatograph comprising a honeycomb substrate comprising a hole for flowing a sample formed therein and a separation phase filled in the hole.

The advantages of the column for a chromatograph according to the present invention will be described below. That is, for example as shown in a schematic cross sectional view of FIG. 1, a separation phase 2 is filled in holes 1a for flowing a sample of a honeycomb substrate 1. The sample is supplied into the inlet 1b of each hole 1a, as an arrow "C", to discharge separated component from each outlet 1c as an arrow "D", so that the separated component is analyzed by means of a detector. According to the column for chromatograph having the above structure, the pore size of each hole 1a can be designed as a sufficiently small value for preventing the diffusion of the sample into multi flow routes. In addition to this, it is possible to improve the amount of the sample and analyze the sample using a common HPLC system, by increasing the number of the holes 1a for flowing a sample.

Moreover, according to the honeycomb substrate 1, it is possible to reduce the deterioration of resolution of separation efficiency even when the whole honeycomb substrate 1 is curved or deformed as shown by arrows "A" and "B." That is, when the whole of the honeycomb substrate is curved or deformed, all the holes 1a for flowing sample are similarly curved or deformed. The sample thus flows in the holes in a substantially similar manner as in a honeycomb substrate that is not curved or deformed.

Contrary to this, when many capillaries 11 are bundled in a column 10 shown in FIG. 2, some capillaries 11A inevitably tend to be inclined. As a result, a time period required for the passage of samples in the capillaries that are held in parallel with each other is different from that of a sample in inclined capillaries, so that the resolution of separation is reduced. Moreover, the spacing between adjacent capillaries tends not to be constant, so that an excess pressure is applied on a part of the bundled capillaries which causes tipping or breakage of the capillaries.

These and other objects, features and advantages of the invention will be appreciated upon reading the following description of the invention when taken in conjunction with the attached drawings, with the understanding that some modifications, variations and changes of the same could be made by the skilled person in the art.

DETAILED DESCRIPTION OF THE INVENTION

Figure 1:
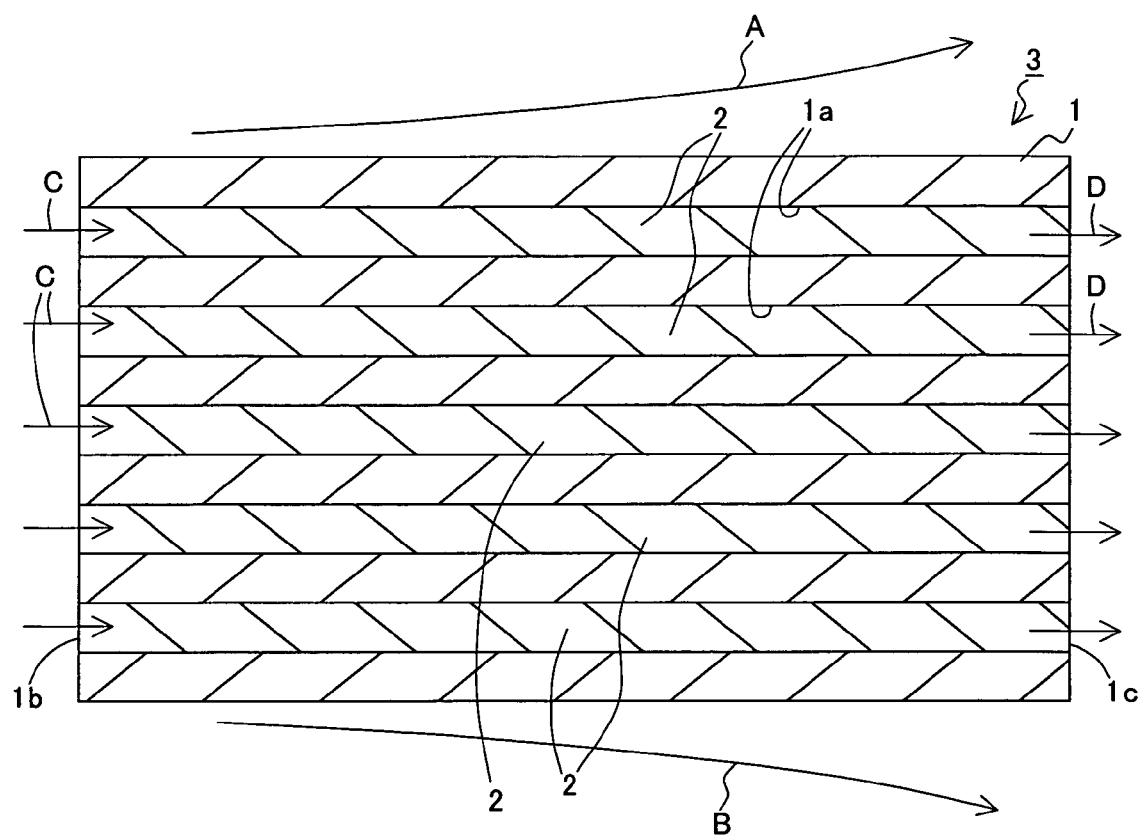
FIG. 1 is a longitudinal cross sectional view schematically showing a column for chromatograph according to an embodiment of the present invention.
Figure 2:
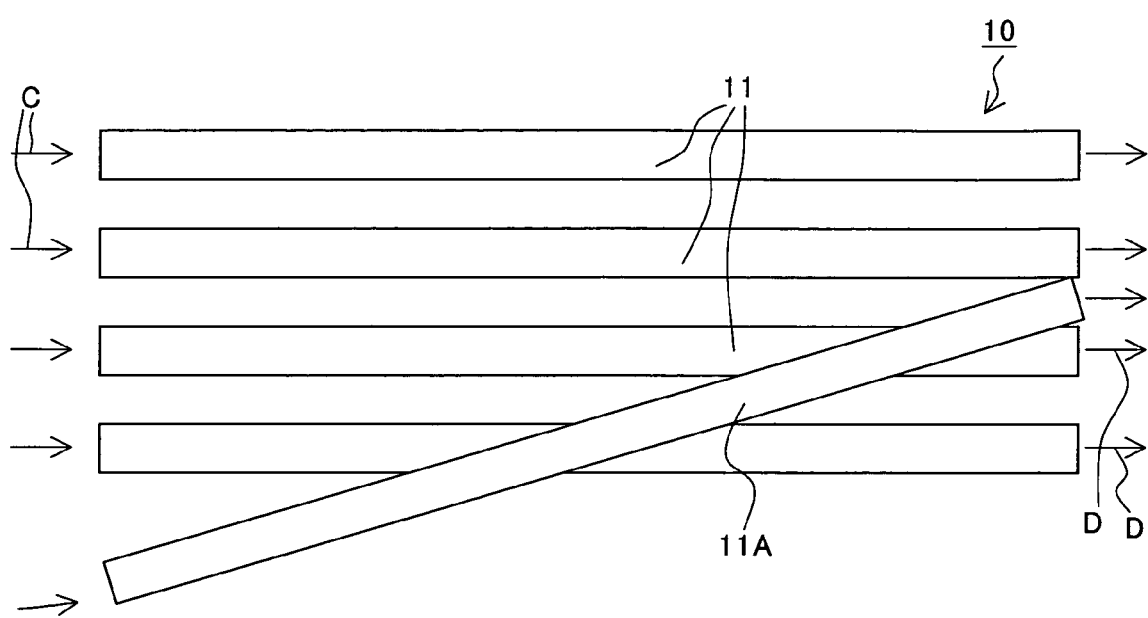
FIG. 2 is a front view schematically showing a column 10 produced by bundling capillaries.

The present invention will be described further in detail below.

The material of the honeycomb substrate is not particularly limited, and may be a ceramic, a metal, a glass, a polymer or a ceramic-metal composite material. The following materials are preferably used. It is preferably an inorganic oxide such as silicon oxide, aluminum oxide, titanium oxide, zirconium oxide and so on, a ceramic such as silicon carbide, silicon nitride and so on, or a material used for a substrate for a column such as stainless steel and PEEK resin.

The pore size of the hole for flowing the samples that are formed in the honeycomb substrate is not particularly limited. As the pore size of the hole for flowing the samples decreases, the diffusion of the sample into many flow routes in the separation phase can be reduced and the resolution of separation can be improved. From this viewpoint, the pore size for flowing a sample is preferably 1 mm or smaller. Further, the pore size of the holes for flowing a sample formed in the honeycomb substrate is preferably at least 0.05 mm, so that the amount of the sample can be increased using a small number of the holes for flowing a sample.

Many kinds of samples may be used as far as the sample is commonly used for a liquid phase chromatograph.

The material for the separation phase that is filled in the holes for flowing a sample is not particularly limited, and may include an organic polymer, such as styrene-divinyl benzene copolymer or the like, and an inorganic particle filler such as silica gel.

Particularly preferably, the separation phase is made of a porous skeleton structure generated by a sol-gel transition accompanied by a phase transition. For performing the reaction, a solution containing a precursor of a network-forming component is produced. The precursor in the solution is then reacted, for example hydrolyzed, to generate a sol, and the sol is gelled (solidified). The process is called "sol-gel transition." Phase transition of a phase that is rich in the network-forming component for causing gellation (gel phase) and a phase that is rich in a solvent component that is irrelevant with respect to gellation (solvent phase) is induced parallel to the sol-gel transition. As a result, the gel forms a network like structure, so that the solvent phase is dried to remove the solvent to obtain the porous body having the open pores.

In the sol-gel reaction system, phase separation occurs over time. That is, the system is separated to a phase that is rich in a network-forming component causing gel formation (gel phase) and a phase that is rich in a solvent component which is irrelevant of the gel formation (solvent phase). In the formation of these phases, each component is diffused inversely with respect to the concentration gradient based on the difference in the chemical potential as the driving force. The movement of substances continues until each phase reaches an equilibrium composition specified at a given temperature and pressure.

After the sol-gel transition reaction is terminated in the solvent, the resulting wet gel is washed or the solvent is exchanged with another solvent. The solvent is then removed to obtain an inorganic porous composite body. If required, the inorganic porous composite body may be heat treated at an appropriate temperature.

When the separation phase is made of a porous skeleton structure that is generated by sol-gel transition accompanied by phase transition, the porous skeleton structure has open pores whose pore size and porosity are properly controlled. Pressure depressions in the separation phase can be thereby reduced.

The pore size (diameter) of the open pores of the porous skeleton structure are preferably 500 nm or more, for reducing the pressure depression of the separation phase used as a column. Such macropores are formed in a region occupied by the solvent phase generated in the phase separation process. In a co-continuous structure, in which the solvent and gel phases are both interconnected, respectively, a considerably sharp size distribution can be obtained.

The inorganic material of which the porous skeleton structure may be made is not particularly limited. A metal oxide is particularly preferred. Suitable examples include silicon oxide and titanium oxide.

The precursor for the network-forming component for causing gellation in the sol-gel reaction includes the following:

(1) A metal alkoxide, a metal complex, a metal salt, a metal alkoxide modified with an organic substance, a metal alkoxide with cross linked organic substance, or an organic metal alkoxide organic replaced with an alkyl group;

(2) A partially hydrolyzed product of a metal alkoxide, a metal complex, a metal salt, a metal alkoxide modified with an organic substance, a metal alkoxide cross linked with an organic substance, or an organic metal alkoxide replaced with an alkyl group;

(3) A polymer product of partial polymerization of a metal alkoxide, a metal complex, a metal salt, a metal alkoxide modified with an organic substance, a metal alkoxide with a cross-linking organic substance, or an organic metal alkoxide partly substituted with an alkyl group; and (4) Sol-gel transition by means of changing the pH of water glass or aqueous solution of the other silicate.

Further, in a more specific manufacturing process, a water soluble polymer is dissolved in an acidic aqueous solution. The precursor, more preferably a metal compound having a hydrolyzable functional group, is then added to the solution to perform hydrolysis. The degree of polymerization of the precursor of the network-forming component is gradually increased so that the miscibility between the gel phase containing the network-forming component and solvent phase containing water as the main component, or solvent phase containing a water soluble polymer as the main component is reduced. During the process, spinodal decomposition is induced parallel to gellation which is proceeded by the hydrolysis and polymerization of the network-forming component in the solvent. The product is then dried and heated.

Any water soluble polymer may be used, as far as it can be used for producing an aqueous solution having an appropriate concentration and may be uniformly dissolved into a reaction system containing an alcohol generated from a metal compound having a hydrolyzable functional group. Specifically, it is preferred to use sodium salt or potassium salt of polystyrene sulfonate as the metal salt of a polymer; polyacrylic acid as an acid of a polymer dissociated to generate a polyanion; polyallyl amine and polyethylene imine as the base of a polymer dissociated to generate a polycation; polyethylene oxide as a neutral polymer having an ether bond in the main chain; or polyvinyl pyrrolidone or the like. Further, instead of an organic polymer, formamide, a polyalcohol, and a surfactant may be used. In this case, glycerin as the polyalcohol and polyoxyethylene alkyl ether as the surfactant are most preferred.

The metal compound having a hydrolyzable functional group may be a metal alkoxide or the oligomer. The alkoxide or oligomer preferably has an alkyl group having a small number of carbon atoms such as methoxy, ethoxy, propoxy group or the like. The metal therefor is that constituting the metal oxide to be finally produced, such as Si, Ti, Zr or Al. One or more metals may be used. On the other hand, the oligomer may be uniformly dissolved or dispersed in an alcohol and specifically the number of repetition may be up to about 10. Further, an alkyl alkoxy silane in which some of the alkoxy groups in a silicon alkoxide are replaced with an alkyl group, and the oligomer having a repetition number up to about 10 may be preferably used. Further, a metal alkoxide replaced with alkyl group containing titanium or the like as the main metal element instead of silicon may be used.

Further, the acidic aqueous solution is preferably 0.001 N or more of a mineral acid, normally hydrochloric acid, nitric acid or the like, or 0.01 N or more of an organic acid such as formic acid, acetic acid or the like.

The hydrolysis and polymerization reactions can be performed by holding the solution at a temperature of room temperature to 40 or 80° C. at 0.5 to 5 hours. The gellation and phase separation may be caused during the process.

An enzyme such as glucose isomerase or the like, a catalyst such as platinum, palladium or the like, or a functional group such as octadecyl group or the like may be supported with the separation phase of the column according to the present invention. The inventive column may be appropriately utilized for a column for a liquid phase chromatograph.

EXAMPLES 5 weight parts of polyvinyl alcohol as a binder was added to 100 weight parts of alumina powder having an average grain diameter of 2 μm and blended with a blender to obtain clay (slurry). The clay was then supplied into an extruder for extrusion at a rate of 10 mm/sec to obtain an elongate body, which was cut at a length of 100 mm each to obtain shaped bodies. The shaped body was introduced into a drier and dried at 120° C. for 10 minutes to obtain a shaped body (dried body) having an outer diameter ϕ of 2.0 mm and 19 holes each having a pore size ϕ of 0.2 mm.

The thus obtained shaped body was sintered according to the following temperature schedule. That is, the temperature was elevated to 200° C. in 1 hour, held at 200° C. for 1 hour, elevated to 300° C. in 1 hour, elevated to 1600° C. in 6 hours, held at 1600° C. for 2 hours for sintering and cooled naturally to room temperature. The resulting sintered body was then removed.

Finally, the thus obtained sintered body was file finished at both end faces and the wastes were removed to obtain a finished body.

Generation of Separation Phase in Holes for Flowing a Sample 0.9 g of polyethylene oxide (supplied by Aldrich Co.) as the water soluble polymer and 1.2 g of urea were uniformly dissolved in 10 ml of 0.01 mol/L acetic acid solution to obtain a solution. After that, the solution was stirred for 10 minutes under cooling with ice, and 5 ml of tetramethoxysilane (a precursor for a network-forming component: supplied by Shin-Etsu Chemical Co., Ltd.) was added under stirring to perform hydrolysis. The thus obtained transparent solution was filled into the holes for flowing a sample. The honeycomb substrate was then held in a constant temperature bath at 40° C. until the solution was solidified. The thus obtained gel was aged for about 24 hours at 40° C. The honeycomb substrate was then held at 110° C. for 4 hours and then dried at 60° C. to evaporate and remove the solvent. After the honeycomb substrate was heat treated at 800° C. to decompose organic substances, silica constituting the separation phase was chemically modified with octadecyl group to obtain a column according to the present invention.

Figure 3:
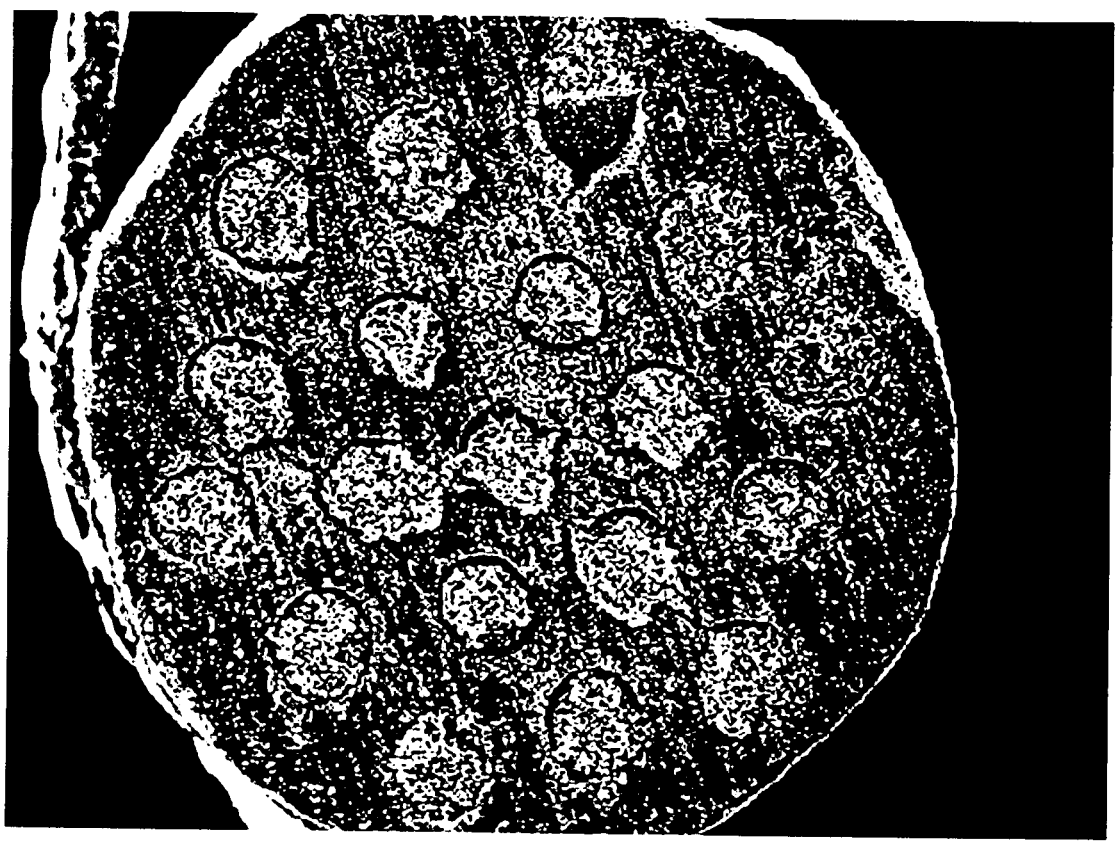
FIG. 3 is a photograph taken by an electron microscope showing a cross section of a column according to one embodiment of the present invention.
Figure 4:
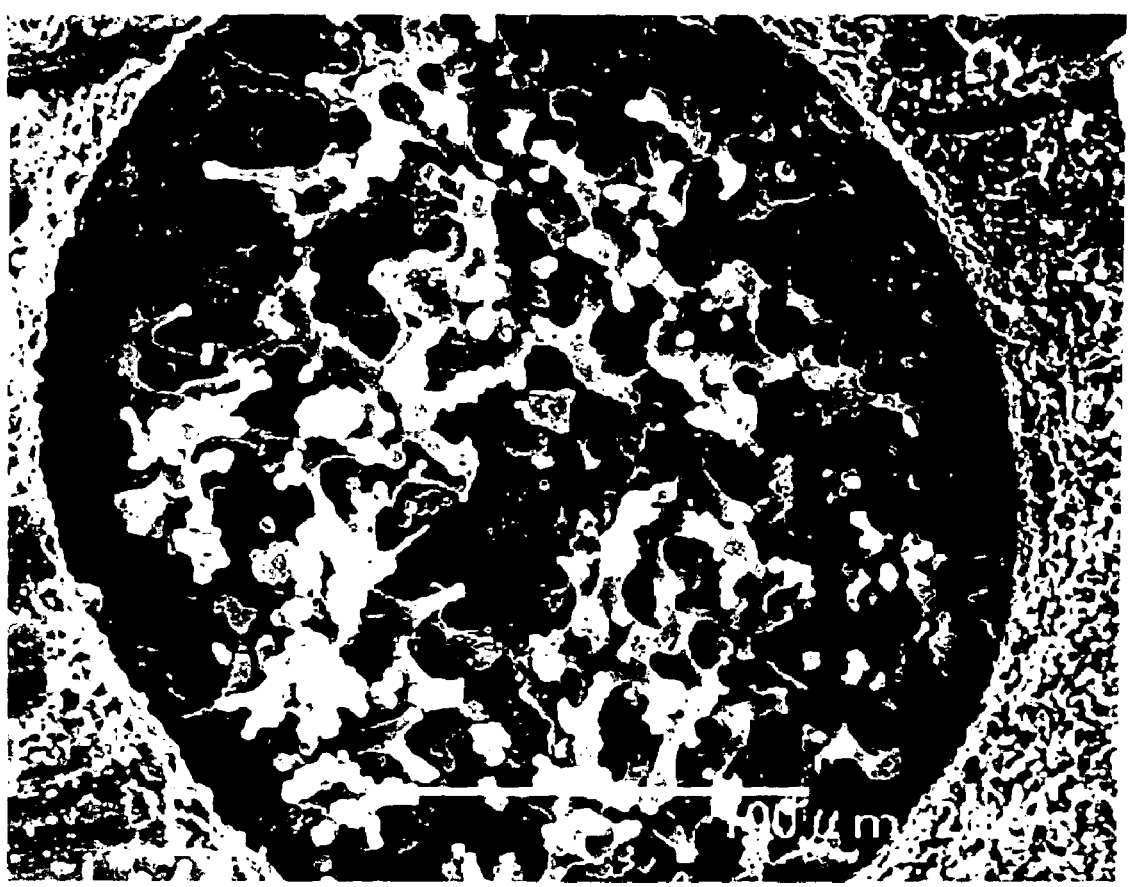
FIG. 4 is an enlarged photograph showing the inside of a hole for flowing a sample shown in FIG. 3.
Figure 5:
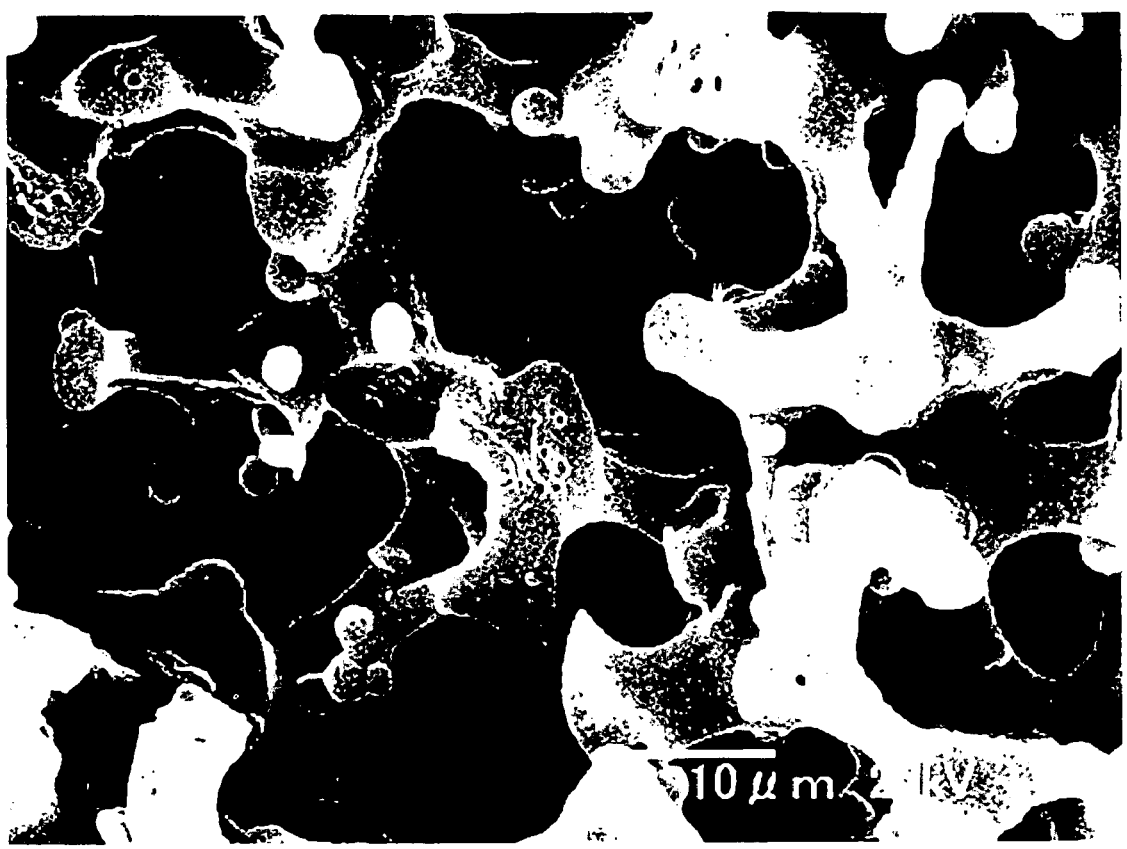
FIG. 5 is an enlarged photograph showing a part of FIG. 4.

FIG. 3 shows a photograph (at a magnitude of 50) taken by an electron microscope of a cross section of the thus obtained column according to the present invention. The column of the present example had 19 holes for flowing a sample. A porous body was generated in each of the holes. FIG. 4 is a photograph showing an enlarged view of the inside of the hole for flowing a sample (at a magnitude of 500). It is observed a microstructure in which silica is continuously formed to network-like or dendritic form. It was further proved that considerably large pores are uniformly formed. FIG. 5 is a photograph showing an enlarged view of a part of FIG. 4 (at a magnitude of 2000).

Experiment of Separation of Sample Components

A liquid chromatograph system was equipped with the thus obtained column. A mixed solution of nitrobenzene and toluene was selected as a sample solution and added as the moving phase. The sample solution flowed into the column, and it was shown that the peaks of nitrobenzene and toluene can be separated.

As described above, the present invention provides a column for a liquid chromatograph having a structure that enables sample separation and maintains a high separation resolution.

The present invention has been explained referring to the preferred embodiments, however, the present invention is not limited to the illustrated embodiments which are given by way of examples only, and may be carried out in various modes without departing from the scope of the invention.

The invention claimed is:

1. A column for a liquid chromatograph comprising:
   a honeycomb substrate including a plurality of holes through which a liquid sample flows; and
   a separation phase comprising a porous body having a continuous porous network structure filling the holes of the honeycomb substrate and forming a substantially uniform pore structure in the holes when viewed in cross-section.

2. The column for a liquid chromatograph of claim 1, wherein said separation phase comprises a porous skeleton structure comprising an inorganic material having open pores formed therein, said porous skeleton structure being generated by a sol-gel transition accompanied by a phase transition.

3. The column for a liquid chromatograph of claim 2, wherein said inorganic material comprises silica.

* * * * *